United States Patent [19]

Confalone et al.

[11] 4,180,659

[45] Dec. 25, 1979

[54] COUMARIN DERIVATIVES TO PRODUCE 8-METHOXYPSORALEN

[75] Inventors: Pasquale N. Confalone; Elizabeth D. Lollar, both of Bloomfield; Giacomo Pizzolato, Belleville; Milan R. Uskokovic, Upper Montclair, all of N.J.

[73] Assignee: Hoffmann-La Roche Inc., Nutley, N.J.

[21] Appl. No.: 947,131

[22] Filed: Sep. 29, 1978

Related U.S. Application Data

[60] Division of Ser. No. 823,257, Aug. 10, 1977, Pat. No. 4,130,568, which is a continuation-in-part of Ser. No. 723,116, Sep. 14, 1976, abandoned.

[51] Int. Cl.$^2$ .................. C07D 311/16; C07D 405/12
[52] U.S. Cl. ................................ 542/427; 260/343.44; 546/256; 546/269

[58] Field of Search .................. 260/343, 44; 546/269, 546/256; 542/427

[56] References Cited

U.S. PATENT DOCUMENTS

| 3,156,697 | 11/1964 | Moffett | 546/269 |
| 3,553,235 | 1/1971 | Kircher et al. | 260/343.44 |

FOREIGN PATENT DOCUMENTS 47-14566  5/1972  Japan .................................. 260/343.44

Primary Examiner—Natalie Trousof
Assistant Examiner—Jane T. Fan
Attorney, Agent, or Firm—Jon S. Saxe; Bernard S. Leon; Frank P. Hoffman

[57] ABSTRACT

The invention relates to synthetic processes to produce the known pharmacologically active 8-methoxypsoralen and derivatives thereof. Also disclosed are various novel intermediates utilized in these processes.

3 Claims, No Drawings

COUMARIN DERIVATIVES TO PRODUCE 8-METHOXYPSORALEN

This is a division of application Ser. No. 823,257 filed Aug. 10, 1977 now U.S. Pat. No. 4,130,568, which is a CIP of Ser. No. 723,116, filed Sept. 14, 1976 now abandoned.

BACKGROUND OF THE INVENTION

It is known that either the topical application or oral ingestion of certain chemical compounds, known as furocoumarins, certain isomers of which are called psoralens, have an effect on the responsiveness of human skin to sunlight. These psoralen compounds, including 8-methoxypsoralen, which has the generic name of methoxsalen, have long been used in the treatment of certain skin diseases, such as vitiligo, which is characterized by a spotty loss of pigmentation of the skin.

The compound 8-methoxypsoralen having the structural formula and the chemical name 9-methoxy-7H-furo[3,2-g][1]benzopyran-7-one has been obtained from natural sources, namely from the fruit of the Ammi Majus Linn. plant, see, for example, Fabmu et al., "Ammi Majus Linn. Pharmacognostical study and isolation of crystalline constituent, Ammoidin", Quart. J. Pharm. and pharmacol., 21:449, 1948.

Similarly, derivatives of 8-methoxypsoralen (methoxsalen) are known in the literature along with their photobiological activity, see, for example, de Souza et al., J. Hetero. Chem., 3, 42–45, (1966) and Antonello, Gazz. Chim. Ital., 88, 415 (1958).

As used herein, the term "lower alkyl" comprehends straight or branched chain hydrocarbon groups having from 1 to 7 carbon atoms, preferably from 1 to 4 carbon atoms, such methyl, ethyl, propyl, isopropyl and the like. The expression "aryl" denotes an aromatic residue such as phenyl, pyridyl, furyl, or a halo or lower alkyl-substituted phenyl residue such as o-tolyl, m-tolyl, p-tolyl, o-chlorophenyl, p-bromophenyl and the like. By the term "aralkyl" is meant a radical in which a lower alkyl H atom is substituted by an aryl group e.g., benzyl or alkoxy, halo, nitro or alkyl substituted benzyl. By the term alkanol is meant an alcohol of 1 to 7 carbon atom, preferably 1 to 4 carbon atoms, which may be straight or branched chain.

The present invention is drawn to synthetic processes to produce the compound 8-methoxypsoralen and derivatives thereof. The following reaction scheme represents the various alternate process steps and novel intermediates which may be utilized to produce methoxsalen (compound of formula VII) or derivatives thereof.

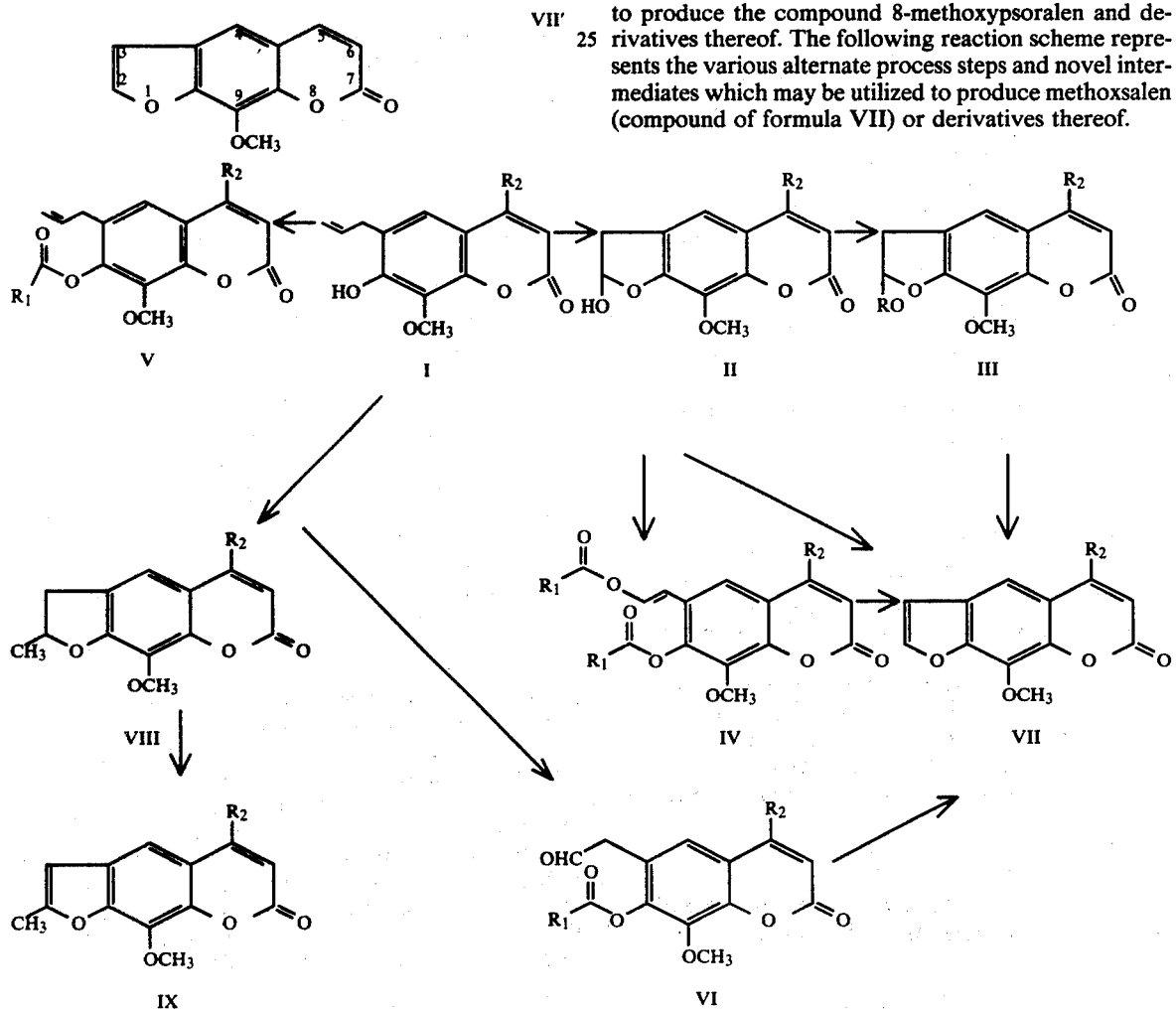

wherein R and $R_1$ is selected from the group consisting of lower alkyl, aryl or aralkyl, and $R_2$ is selected from the group consisting of hydrogen, lower alkyl, aryl or aralkyl.

I→II

The starting material of formula I wherein $R_2$ is hydrogen or methyl are known compounds, see, for example, de Sovza et al., J. Hetero. Chem. 3, 42–45 (1966) and wherein $R_2$ is lower alkyl other than methyl, aryl or aralkyl are novel compounds and can be obtained following the procedures set forth in the above reference in an analogous manner.

The starting material (I) is reacted with an alkali metal periodate, such as sodium, or potassium periodate in the presence of an osmium tetroxide catalyst to produce a compound of formula II. Solvents suitable for such a reaction include preferably a one phase aqueous-organic solvent system, e.g., an aqueous lower alkanol or a two phase system, such as ethylacetate-water or benzene-water. The temperature at which such a reaction may be affected ranges from 0° C. to 50° C. with room temperature preferred. The above oxidative cyclization is preferably run at atmospheric pressure.

II→III

The compound of Formula II may be reacted thereafter in the presence of an organic or inorganic catalyst such as hydrogen chloride or toluene sulfonic acid with a variety of aliphatic or aromatic alcohols dependent on which specific substituent is desired. For example, where R is lower alkyl, alcohols such as methanol (R=methyl), ethanol (R=ethyl), propanol (R=propyl) and so on, are chosen. Where R is aryl, then the alcohol chosen would be a phenol e.g., phenol or halo, nitro or alkyl substituted phenol and where R is aralkyl then a benzyl alcohol such as benzyl alcohol or halo, nitro or alkyl substituted benzyl alcohol would be utilized. The reaction is affected at a temperature range of from 0° C. to reflux temperature with room temperature preferred. Where an alcohol is a solid at room temperature a co-solvent may be utilized, such as, methylene chloride to carry out the reaction.

II or III→VII

The compounds of Formula II or III are thereafter reacted with an acid strong enough to cleave the hydroxy (II) or ether (III) group from the fused furan ring and yet induce unsaturation between the 2,3-position of the benzopyran-7-one (VII) compound. Suitable acids include formic acid which is preferred, orthophosphoric acid and benzene-toluene sulfonic acid. The reaction temperature ranges from room temperature to 100° C. with a range of 70° C. to 100° C. as preferred and a temperature of 90° C. considered as an optimum reaction temperature.

II→IV

The compound of Formula II is reacted with an acid anhydride, i.e., a compound of the formula

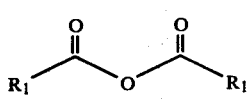

wherein $R_1$ is selected from the group consisting of lower alkyl, aryl and aralkyl or an acid chloride, i.e., a compound of the formula

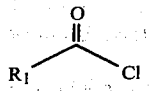

wherein $R_1$ is selected from the group consisting of lower alkyl, aryl and aralkyl.

The reaction is affected in the presence of an organic base such as pyridine, triethylamine, aniline, piperidine and pyrollidine and the like, at a temperature of from room temperature to 100° C. with room temperature preferred.

IV→VII

A compound of the formula IV is reacted with a strong aqueous mineral acid such as sulfuric acid or preferably orthophosphoric acid. The reaction may be affected at a temperature of from room temperature to 100° C. preferably 70° C. to 100° C. with 90° C. being the most preferable reaction temperature.

I→V

A compound of formula V is produced by reacting a Formula I compound with an acid anhydride, i.e., a compound of the formula

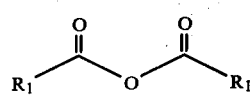

wherein $R_1$ is selected from the group consisting of lower alkyl, aryl and aralkyl, or an acid chloride, i.e., a compound of the formula

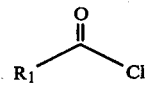

wherein R is as above.

The reaction is affected in the presence of an organic base, such as pyridine, triethylamine, aniline, piperidine or pyrollidine at a temperature range of from room temperature to 100° C. with room temperature preferred.

V→VI

The compound of formula VI is produced by reacting a compound of Formula V with an alkali metal periodate, such as, sodium or potassium periodate in the presence of an osmium tetroxide catalyst. Solvents suitable for the reaction include, preferably, a two phase organic solvent-water system, e.g., ethyl acetate-water. Other suitable two phase systems would include benzene-water and toluene-water systems. In addition a one-phase aqueous lower alkanol. The temperature at which such a reaction may be carried out ranges from 0° C. to 50° C. with room temperature preferred. The reaction is preferably run at atmospheric pressure.

VI→VII

A compound of the Formula VII is produced by the reaction of a compound of the Formula VI with a strong acid, preferably a strong aqueous mineral acid such as sulfuric acid, hydrochloric acid, nitric acid, or preferably orthophosphoric acid. The reaction may be carried out at a temperature of from room temperature to 100° C. preferably 70° C. to 100° C. with 90° C. being the most preferable reaction temperature.

I→VIII

A compound of formula I is triturated in an acid catalyzed reaction, preferably with sulfuric acid. Other acids useful for this reaction include toluene sulfonic acid, orthophosphoric acid and other concentrated mineral acids. The reaction temperature may be varied from 25° C. to 100° C. with room temperature being preferred.

VIII→IX

The compound of the Formula VIII is thereafter dehydrogenated to a compound of the Formula IX for example by exposure to high temperatures in the presence of a noble metal catalyst. A temperature range of 100° C. to 300° C. with reflux temperature of the solvent being preferred is utilized. Solvents utilized in such a reaction include high boiling ethers, preferably such as aromatic ethers, e.g., diphenyl ether in conjunction with noble metal catalyst, such as, platinum or palladium. In addition, heating the compound of Formula VIII in the presence of various quinones, such as chloranil or 2,3-dichloro-5,6-dicyano-1,4-benzoquinone in an inert organic solvent such as xylene may also be used.

Compounds of the formulae II, III, IV, V, VI and VIII represent novel compounds which are useful as intermediates in the production of compounds of the formulae VII and IX. The compound of the formula VII having the common name methoxsalen or 8-methoxypsoralen has demonstrated utility as an agent in the treatment of vitiligo, a disease which manifests itself in the loss of pigmentation in the epidermal cell of the body, see, for example, articles by Lerner et al., Journal of Investigative Dermatology, Vol. 20, No. 4, pages 299–314, 1953; or Kanof, Journal of Investigative Dermatology, Vol. 32, No. 2, pages 343–344, 1959, and as an antipsoriasis agent.

The compounds of formulae VII and IX have also demonstrated photobiological activity which it is thought is linked to antipsoriatic activity. The following testing was carried out on the compound of formulae VII and preferred compounds of formula IX.

Compounds of formulae IX and VII were dissolved in ethanol. The backs of albino guinea pigs were eiplated. The entire back was demarked with ten exposure windows, each 2.5×2.5 cm. in size. The test compounds were applied in each of these ten windows. Each compound was tested in the following concentration range: 2.5, 5, 10, 15, 20, 50, 100, 200 $\mu g/6.25$ sq. cm.

On each test animal two 2.5×2.5 sites were used as controls. (One site received 16 $J/cm^2$ ultraviolet light and the other site was left covered during the exposure period.) One hour after application of the test compounds, the animals were exposed to a longwave ultraviolet light source emitting 320–400 nm radiation, at a distance of 5–7.5 cm between the lamp and the back of the animal. Each animal received an ultraviolet irradiance dose of 16 $J/cm^2$ which was delivered in approximately 1 hour and 15 minutes. During the topical application and irradiation period, the animals were immobilized on a wooden board. At 24 and 48 hours after exposure, the animals were examined for the degree of redness and edema. The degree of redness was assessed visually as well as by measuring the skin reflectance with a photovolt reflectance meter. If a compound shows positive photosensitization reaction at 2.5 $\mu g/cm^2$ and exhibits + to ++ grade, it is considered markedly reactive, and the one that shows a trace erythema at 25 or 50 $\mu g/cm^2$ is considered moderately reactive. A compound which shows no erythema response even at 500 to 1,000 $\mu g/cm^2$ concentration is considered inactive or non-photosensitizing.

In the above set, the compounds of formulae VII and IX (2-methyl-9-methoxypsoralen, 5-methyl-9-methoxypsoralen and 2,5-dimethyl-9-methoxypsoralen) exhibited potent photosensitizing activity; including marked erythema and edema reactions at very low concentrations (5–20 and 20–50 $g/6.25$ $cm^2$, respectively).

Compounds of the formulae VII and IX may be administered either orally or topically. For oral treatment of psoriasis, the active ingredient is generally formulated in tablets or in gelatin capsules. A typical tablet formulation, for example, may consist of the following ingredients:

| | |
|---|---|
| Formula VII or IX Compound, fine powder | 20.4 grams |
| Polysorbate 80 | 1.0 grams |
| Microcrystalline Cellulose PH 101 | 40.0 grams |
| Corn Starch, USP | 25.0 grams |
| Magnesium Stearate | 1.6 grams |
| Lactose, Direct Tablet Grade | 212.0 grams |

The active ingredient was thoroughly blended in a suitable mixer with the tablet excipients and compressed on a single punch tablet machine into 1000 tablets, each weighing 300 mg. and containing 20 mg. of either the formula VII or IX compound as active ingredient.

A typical gelatin capsule formulation, for example, may consist of the following ingredients:

| | |
|---|---|
| Formula VII or IX Compound, fine powder | 20.4 grams |
| Corn Starch, USP | 199.6 grams |

The active ingredient was thoroughly mixed with the starch and filled into 1000 #3 two-piece hard gelatin capsules, each capsule containing 220 mg. of the mixture which represents 20 mg. of the formula VII or IX compound per capsule.

The general oral dosage regimen will include from about 10 mg. to about 50 mg. per kg. of body weight. A dose of about 20 mg. per kg. is generally preferred.

Tablets incorporating the compounds of formulae VII and IX are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents again include starch and lactose while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps, and polyethylene glycol.

Capsules are readily produced by filling gelatin capsules with any desired form of the desired formula VII or IX compounds. If desired, the compounds can be diluted with an inert powdered diluent, such as a sugar, starch, or purified crystalline cellulose in order to increase its volume for convenience in filling capsules.

Compounds of the formulae VII or IX may also be utilized as solutions or ointments in the treatment of psoriasis. A typical solution and ointment would be as follows:

| Solution | |
|---|---|
| Formula VII or IX Compound | 1.02 grams |
| Butylated Hydroxytoluene (BHT) | 0.1 grams |
| Acetone | 20.0 ml. |
| Propylene Glycol | 5.0 ml. |
| Ethanol 95%, enough to make | 100 ml. |

The active ingredient was dissolved in a 50 ml. mixture of ethanol (25 ml.)/acetone (20 ml.)/propylene glycol (5.0 ml.) in a flask heated on a water bath, the BHT (antioxidant) was added and dissolved, then the solution allowed to cool to room temperature at which time the ethanol was added to make the final volume 100 ml.

| Ointment | |
|---|---|
| Formula VII or IX Compound, Micronized | 10.0 grams |
| Hydrophilic Petrolatum USP qs. ad | 1000 grams |

To 990 grams of hydrophilic petrolatum melted on a steam bath, the active ingredient was added with constant stirring until uniformly dispersed. The mixture was removed from the steam bath and stirred constantly until the ointment congealed. The final product may be put through a roller mill to further insure adequate dispersion of the formula VII or IX compound.

In the case of topical application, the active ingredient is generally formulated as an ointment or as a solution. Ointments and solutions for topical administration can be formulated with any of a number of pharmaceutically acceptable carriers, including animal and vegetable oils, mixtures of waxes, solid and liquid hydrocarbons, glycols, and the like.

The following Examples serve to illustrate the instant invention, but are not to be construed as limiting said invention.

EXAMPLE 1

A solution of 52.2 g. (0.225 mole) of 6-allyl-7-hydroxy-8-methoxycoumarin[1] in 540 ml. of methanol was placed in a 3 l. three-necked flask and equipped with a mechanical stirrer. To this solution, 270 ml. of distilled water was added (exothermic), and the reaction was cooled back to room temperature. At this poing, the mechanical stirring was begun and 128.7 g. (0.600 mole) of potassium periodate was added, followed by 9 ml. of a 10% aqueous solution of osmium tetroxide (10 mg/ml). The mixture turned dark immediately, but became yellow as the reaction proceeded. After a total of 2.5 hours, the mixture was treated with 600 ml. of methylene chloride and then stirred for 5.0 min. The suspended solid was filtered and triturated with 5×200 ml. portions of hot methylene chloride/methanol, 80:2. The supernatant from each trituration was added to the original filtrate, and the mixture was transferred to a separatory funnel containing one liter of brine. After thorough shaking, the organic layer was separated and the aqueous phase was further extracted with 3×300 ml. portions of methylene chloride/methanol, 80 20. The organic phases were further washed once with brine, dried over sodium sulfate, and evaporated to yield 2-hydroxy-9-methoxy-2,3-dihydro-7H-furo[3,2-g][1]benzopyran-7-one, mp 135°–137°. The compound may be further purified by recrystallization from ethyl acetate to afford pure product, mp 137°–138°.

[1]Prepared according to T. R. Seshadri and M. S. Sood, Indian J. Chem., 1, 291–294 (1963).

EXAMPLE 2

Dry methanol was saturated at 0° with gaseous hydrogen chloride. A sample of 0.576 g. (2.46 mmoles) of 2-hydroxy-9-methoxy-2,3-dihydro-7H-furo[3,2-g][1]benzopyran-7-one was dissolved in the resultant solution, and the dark reaction was allowed to proceed at room temperature for one hour. The solvent was evaporated and the residue was taken up in ethyl acetate/benzene. 1:4 and filtered through 50 g. silica, eluting with the same solvent system. Fractions containing the product, which is first eluted, were combined and evaporated to give pure 2,9-dimethoxy-2,3-dihydro-7H-furo[3,2-g][1]benzopyran-7-one as a white solid. Recrystallization from methanol afforded an analytical sample of this product, mp 131°–132°.

EXAMPLE 3

A sample of 0.157 mg. (0.67 mmole) of 2-hydroxy-9-methoxy-2,3-dihydro-7H-furo[3,2-g][1]benzopyran-7-one in 3 ml. of acetic anhydride/pyridine, 1:1 was stirred at 25° for one hour. The solvents were evaporated and the residue was chromatographed on thick layer silica plates, eluting with benzene/ethyl acetate, 4:1. The product was found at $r_f$=0.4. Isolation led to pure 7-acetoxy-6-[2-acetoxyvinyl]-8-methoxycoumarin, mp 140° (dec.).

EXAMPLE 4

Absolute ethanol was saturated with gaseous hydrogen chloride at 0°. To this solution, 5.0 g. (0.214 mole) of 2-hydroxy-9-methoxy-2,3-dihydro-7H-furo[3,2-g][1]benzopyran-7-one was added, and the reaction was allowed to proceed at 25° for 2.0 hours. The solvent was evaporated, and the residue was passed through a column consisting of 150 g. silica (upper layer) and 50 g. of neutral alumina (lower layer) using benzene/ethyl acetate, 4:1. Fractions containing the product were combined and evaporated to afford pure 2-ethoxy-9-methoxy-2,3-dihydro-7H-furo[3,2-g][1]benzopyran-7-one as a white solid. Recrystallization from ethanol yielded an analytical sample, mp 119°–120°.

EXAMPLE 5

A solution of 40 mg. (0.13 mmole) of 7-acetoxy-6-[2-acetoxyvinyl]-8-methoxycoumarin in 5 ml. of 85% phosphoric acid was heated at 90° for 30 minutes. The solution was cooled and partitioned between water/methylene chloride. The aqueous phase was further extracted with methylene chloride. The organic phases were combined, dried over sodium sulfate, and evaporated to afford pure 9-methoxy-7H-furo[3,2-g][1]benzopyran-7-one, mp 145°–146°, as a crystalline white solid.

EXAMPLE 6

A solution of 100 mg. (0.38 mmole) of 2-ethoxy-9-methoxy-2,3-dihydro-7H-furo[3,2-g][1]benzopyran-7-one in 2 ml. of formic acid was heated at 100° for 30 min. The reaction was cooled and evaporated to leave a residue which was filtered through alumina using benzene/ethyl acetate, 4:1 to yield, upon evaporation of the filtrate, pure 9-methoxy-7H-furo[3,2-g][1]benzopyran-7-one, mp 145°–146°.

EXAMPLE 7

A solution of 0.253 g. (1.02 mmoles) of 2,9-dimethoxy-2,3-dihydro-7H-furo[3,2-g][1]benzopyran-7-one in 10 ml. of formic acid was heated at 100° for 40 min. The reaction was cooled and evaporated. The residue was filtered through alumina using benzene/ethyl acetate, 4:1 to yield, upon evaporation of the filtrate, pure 9-methoxy-7H-furo[3,2-g][1]benzopyran-7-one, mp 145°–146°.

EXAMPLE 8

A solution of 2.32 g. (0.010 mole) of 6-allyl-7-hydroxy-8-methoxycoumarin in 8 ml. of chloroform was treated with 4.5 ml. of acetic anhydride/pyridine, 1:2. The reactants were stirred at 25° for 2.0 hours and then partitioned between 1 N HCl/methylene chloride. The aqueous phase was further extracted with methylene chloride. The organic extracts were combined, dried over sodium sulfate, and evaporated to afford pure 7-acetoxy-6-allyl-8-methoxycoumarin as a white solid, mp 101°–102°. Recrystallization from ethanol afforded an analytical sample, mp 102°14 103°.

EXAMPLE 9

A solution of 0.274 g. (0.001 mole) of 7-acetoxy-6-allyl-8-methoxycoumarin in 10 ml. EtOAc/water, 1:1 was treated with 0.8 g. (0.0033 mole) of potassium periodate and 0.5 ml. of a 10% aqueous solution of osmium tetroxide (10 mg. $OsO_4$/ml $H_2O$). The reactants were stirred at 25° for 5.0 hours. The organic layer was separated, and the aqueous phase was further extracted with ethyl acetate. The organic extracts were combined, dried over sodium sulfate, and evaporated to yield pure 7-acetoxy-8-methoxycoumarin-6-acetaldehyde as a colorless oil.

EXAMPLE 10

A solution of 2.76 g. (0.010 mole) of 7-acetoxy-8-methoxycoumarin-6-acetaldehyde in 30 ml. of 85% phosphoric acid was heated at 100° for 20 min, cooled and partitioned between water/methylene chloride. The aqueous phase was further extracted with methylene chloride. The organic extracts were combined, dried over sodium sulfate, and evaporated to yield 9-methoxy-7H-furo[3,2-g][1]benzopyran-7-one. Purification was achieved by filtration through a silica gel column, eluting with benzene/ethyl acetate, 4:1. The filtrate was evaporated to afford pure end product, mp 145°–146°.

EXAMPLE 11

A sample of 1.0 g. (4.31 mmoles) of 6-allyl-7-hydroxy-8-methoxycoumarin was dissolved in 20 ml. of conc. sulfuric acid at 25°. After 10 min, the solution was diluted with ice water. The mixture was extracted with methylene chloride, dried over sodium sulfate, and evaporated to yield 90 g. of residue. This was filtered through a column of silica gel, eluting with benzene/ethyl acetate, 4:1, to afford, upon evaporation of the filtrate, pure 2-methyl-9-methoxy-2,3-dihydro-7H-furo[3,2-g][1]benzopyran-7-one as a white solid. Recrystallization from ethanol yielded an analytical sample, mp 115°–116°.

EXAMPLE 12

To a solution of 0.70 g. (3.02 mmoles) of 2-methyl-9-methoxy-2,3-dihydro-7H-furo[3,2-g][1]benzopyran-7-one in 15 ml. of diphenyl ether was added 0.70 g. of 10% Pd/C. The mixture was heated under reflux for 6.0 hours, cooled, and filtered over Celite (washing with methanol). The methanol was removed from the filtrate by rotary evaporation, and the remaining solution of the product in diphenyl ether was diluted with 200 ml. of pet. ether. After standing overnight, the solid which separated was filtered off and washed with pet. ether to yield 9-methoxy-2-methyl-7H-furo[3,2-g][1]benzopyran-7-one. Recrystallization from ethanol afforded an analytical sample, mp 149°–150°.

EXAMPLE 13

A solution of 52.2 g. (0.223 mole) of crude 2-hydroxy-9-methoxy-2,3-dihydro-7H-furo[3,2-g][1]benzopyran-7-one in 900 ml of 98% formic acid was heated under argon at 100° for 45 min. The solvent was removed in vacuo and the dark residue crystallized. After drying on the high vac, the crude product, was taken up in the minimum amount of warm methylene chloride and filtered through an alumina column. Evaporation of fractions afforded pure methoxsalen, mp 145°–146°.

EXAMPLE 14

A sample of 15.0 g (0.0612 mol) of 6-allyl-7-hydroxy-8-methoxy-4-methylcoumarin was treated with 30 ml of conc. sulfuric acid at 25°. After 10 min, the dark mixture was diluted with 400 ml of ice water and extracted three times with methylene chloride/methanol, 4:1. The organic phases were dried and evaporated; the residue was filtered through 250 g silica, diluting with ethyl acetate/benzene, 1:4 to afford pure 2,5-dimethyl-9-methoxy-2,3-dihydro-7H-furo[3,2-g][1]-benzopyran-7-one, m.p. 113°–115°, as a white crystalline solid. Recrystallization from ethanol gave an analytical sample, m.p. 114°–115°.

EXAMPLE 15

A solution of 10.36 g (0.0422 mol) of 2,5-dimethyl-9-methoxy-2,3-dihydro-7H-furo[3,2-g][-1]benzopyran-7-one in 150 ml of diphenyl ether was treated with 6.0 g of 10% palladium on charcoal. The mixture was heated under reflux for 5.0 hrs, cooled, and filtered over celite. The catalyst was further washed with methanol, and the filtrate was then concentrated to remove the methanol. The residue was diluted with 1.5 l. of pet. ether and stirred overnight. The product was filtered, washed with pet. ether, dried, and passed through a silica column, eluting with ethyl acetate/benzene, 1:4, to yield pure 9-methoxy-2,5-dimethyl-7H-furo[3,2-g][1]benzopyran-7-one, m.p. 154°–155° (ethanol).

EXAMPLE 16

A solution of 2.0 g (8.12 mmols) of 6-allyl-7-hydroxy-8-methoxy-4-methylcoumarin in 20 ml of methanol was treated (mechanical stirring) with 10 ml of water, 5.0 g potassium periodate, and 1.0 ml of a 10% aqueous solution of osmium tetroxide (10 mg/ml). After 3.5 hrs, the mixture was partitioned between water/methylene chloride. The aqueous phase was further extracted with methylene chloride. The organic extracts were dried and evaporated to yield 2-hydroxy-9-methoxy-5-methyl-2,3-dihydro-7H-furo[3,2-g][1]benzopyran-7-one. The compound was dissolved in 40 ml of 98% formic acid and heated under reflux for 1.0 hr. The solution was cooled and evaporated to dryness. The residue was chromatographed over silica, eluting with ethyl acetate/benzene, 1:4, to afford pure 9-methoxy-5-methyl-7H-furo[3,2-g][1]benzopyran-7-one, m.p. 167°–168° (ethanol).

What is claimed

1. A compound of the formula

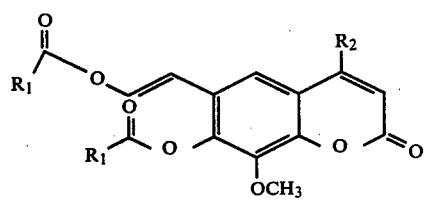

wherein $R_2$ is selected from the group consiting of hydrogen, lower alkyl, phenyl, pyridyl, furyl, halo or lower alkyl substituted phenyl, benzyl and alkoxy, halo, nitro or lower alkyl substituted benzyl and $R_1$ is selected from the group consisting of lower alkyl, phenyl, pyridyl, furyl, halo or lower alkyl substituted phenyl, benzyl and alkoxy, halo, nitro or lower alkyl substituted benzyl.

2. A compound of the formula

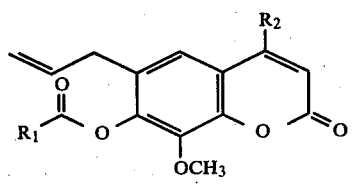

wherein $R_2$ is selected from the group consisting of hydrogen, lower alkyl, phenyl, pyridyl, furyl, halo or lower alkyl substituted phenyl, benzyl and alkoxy, halo, nitro or lower alkyl substituted benzyl and $R_1$ is selected from the group consisting of lower alkyl, phenyl, pyridyl, furyl, halo or lower alkyl substituted phenyl, benzyl and alkoxy, halo, nitro or lower alkyl substituted benzyl.

3. A compound of the formula wherein $R_2$ is selected from the group consisting of hydrogen, lower alkyl, phenyl, pyridyl, furyl, halo or lower alkyl substituted phenyl, benzyl and alkoxy, halo, nitro or lower alkyl substituted benzyl and $R_1$ is selected from the group consisting of lower alkyl, phenyl, pyridyl, furyl, halo or lower alkyl substituted phenyl, benzyl and alkoxy, halo, nitro or lower alkyl substituted benzyl.

* * * * *